(12) United States Patent
Bortlik et al.

(10) Patent No.: US 7,588,781 B2
(45) Date of Patent: Sep. 15, 2009

(54) METHOD FOR INCREASING BIOAVAILABILITY OF LIPOPHILIC BIOACTIVE COMPOUNDS

(75) Inventors: Karlheinz Bortlik, Savigny (CH); Francoise Saucy, Blonay (CH); Eliane Duruz, Epalinges (CH); Myriam Richelle, Savigny (CH); Pierre Lambelet, Saint-Legier (CH); Markus Baur, Aran (CH); Andrea M. A. Pfeifer, Saint-Legier (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 11/553,847

(22) Filed: Oct. 27, 2006

(65) Prior Publication Data

US 2007/0071830 A1    Mar. 29, 2007

Related U.S. Application Data

(60) Division of application No. 10/057,660, filed on Jan. 25, 2002, which is a continuation-in-part of application No. PCT/EP01/06145, filed on May 29, 2001.

(30) Foreign Application Priority Data

May 30, 2000 (EP) .................................. 00111542

(51) Int. Cl.
*A61K 9/00* (2006.01)
*A61K 35/20* (2006.01)
*A61K 36/00* (2006.01)

(52) U.S. Cl. ...................... 424/535; 424/400; 424/520; 424/725; 424/755; 424/757

(58) Field of Classification Search ................. 424/400, 424/725, 755, 757, 520, 535
See application file for complete search history.

(56) References Cited

U.S. PATENT DOCUMENTS

| 4,522,743 | A | | 6/1985 | Horn et al. | |
|---|---|---|---|---|---|
| 5,601,760 | A | | 2/1997 | Rosenberg | |
| 5,643,623 | A | * | 7/1997 | Schmitz et al. | ............... 426/73 |
| 5,705,526 | A | | 1/1998 | Fujiwara et al. | |
| 5,706,526 | A | | 1/1998 | Huang | |
| 5,855,892 | A | | 1/1999 | Potter et al. | |
| 6,203,805 | B1 | | 3/2001 | Collins et al. | |
| 6,235,315 | B1 | | 5/2001 | Runge et al. | |
| 2002/0107292 | A1 | | 8/2002 | Bortlik et al. | |

FOREIGN PATENT DOCUMENTS

| EP | 0278284 | 1/1994 |
|---|---|---|
| EP | 0986963 | 3/2000 |
| GB | 1521691 | 8/1978 |
| WO | WO0191588 | 12/2001 |

* cited by examiner

*Primary Examiner*—Ruth A Davis
(74) *Attorney, Agent, or Firm*—K&L Gates LLP

(57) ABSTRACT

A primary composition that includes at least one lipophilic bioactive compound and a whey protein in an amount effective to increase the bioavailability of the lipophilic bioactive compound, and methods of forming the same. Also, an oral composition that contains the primary composition in a foodstuff, in a food supplement, in a cosmetic preparation or in a pharmaceutical preparation, and methods of forming the same.

17 Claims, No Drawings

METHOD FOR INCREASING BIOAVAILABILITY OF LIPOPHILIC BIOACTIVE COMPOUNDS

CROSS-REFERENCE TO RELATED APPLICATIONS

This application is divisional of patent application Ser. No. 10/057,660, filed Jan. 25, 2002, which is a continuation-in-part of the U.S. national stage designation of International application no. PCT/EP01/06145 filed May 29, 2001, the entire contents of which are expressly incorporated herein by reference.

TECHNICAL FIELD

The present invention relates to a primary composition comprising a lipophilic bioactive compound and to an oral composition comprising the primary composition and its process of preparation.

BACKGROUND

Compositions available on the market that include a lipophilic bioactive compound, namely lycopene, are already known. Lycopene is a natural product which is known to have multiple roles, in particular that of an antioxidant. Lycopene is present in various natural products, in particular tomatoes, melons, guavas and grapefruit. The composition generally available on the market which comprises lycopene is an oleoresin. The problem with this oleoresin is that it has been found that the lycopene present therein is insufficiently bioavailable.

For example, European patent 278 284 relates to a pulverulent composition comprising a synthetic carotenoid. The problem with this composition is that it cannot be used in the food field and, moreover, it is envisaged for a coloring purpose.

Thus, there is a need for a lycopene-containing product which has better bioavailability than the products currently on the market.

SUMMARY OF THE INVENTION

A primary composition that includes at least one lipophilic bioactive compound and a whey protein in an amount effective to increase the bioavailability of the lipophilic bioactive compound. The lipophilic bioactive compound is advantageously obtained, extracted, enriched or purified from a plant, microorganism, yeast or product of animal origin.

The preferred form of the primary composition is as an additive in a foodstuff for oral administration, such as in a food supplement, in a cosmetic preparation or in a pharmaceutical preparation.

The invention also relates to methods of forming the primary composition, the food supplement, cosmetic preparation or pharmaceutical preparation containing the same, and to a method for protecting skin tissue against ageing by administering to a subject in need of such protection one of the primary, oral, or cosmetic compositions disclosed herein.

The process for the preparation of a primary composition comprises associating the whey protein with the lipophilic bioactive compound under conditions sufficient to form the composition a mixture. The composition may be formed by dissolving the whey protein in water to form a first solution, dissolving the lipophilic bioactive compound in a solvent to form a second solution, combining the two solutions, and evaporating the solvent to form the composition as a dispersion. Alternatively, the composition may be formed by mixing the lipophilic bioactive compound with a solvent to form a first mixture, mixing the first mixture with the whey protein in the form of a powder to form a second mixture and evaporating the solvent from the second mixture to produce the composition as a dry powder.

DETAILED DESCRIPTION OF THE INVENTION

The present invention relates to a primary composition comprising a lipophilic bioactive compound and a whey protein. The term "bioactive compound" is understood to mean a compound having a beneficial effect on the human or animal metabolism. The present invention now makes available to the consumer an improved composition obtained from natural products. As will be explained further below, protection and enhancement of the lipophilic bioactive compound is also targeted according to the invention.

The lipophilic bioactive compound is obtained, extracted, enriched or purified starting from a plant, microorganism, yeast or product of animal origin. The term "obtained" is understood to mean that the bioactive product is directly available commercially. The term "extracted" is understood to mean that the bioactive principle has been extracted. The term "enriched" is understood to mean that the non-bioactive compounds have been separated as much as possible. The term "purified" is understood to mean that only the bioactive compound is recovered.

In the case of a bioactive compound originating from a plant, the plant is chosen from the group consisting of tomatoes (i.e., whole tomato, tomato extract, tomato flesh, tomato puree, tomato skin, with or without the seeds), soya, green tea, green coffee beans, spices such as ginger or others, grapes, cocoa and cereals. The microorganism can be any type of bacterium which produces a lipophilic bioactive compound. For example, a probiotic microorganism, in particular a lactic acid bacterium, can be envisaged as microorganism. The yeast can be any yeast which produces a lipophilic bioactive compound, for example a *Saccharomyces*. The product of animal origin is chosen from the group consisting of a liver extract and a milk fraction. The term "milk fraction" is understood to mean any part of the milk.

In the primary composition according to the invention, the lipophilic bioactive compound is chosen from the group consisting of carotenoids, polyphenols, lipophilic vitamins, flavonoids, isoflavones, curcuminoids, ceramides, proanthocyanidins, terpenoids, sterols, phytosterols, sterol esters, tocotrienols, squalene and retinoids, alone or as a mixture. Carotenoids are present in particular in tomatoes, carrots, yellow peaches, apricots and oranges. Lycopene is a carotenoid which is particularly favored in the present composition. Polyphenols are present in particular in green tea, coffee, cocoa or red wine. Lipophilic vitamins are present in particular in numerous vegetables. Flavonoids and isoflavones are present in particular in soya, tea, onions or wine. Curcuminoids are present in particular in ginger. Ceramides are glycolipids present in particular in yeast derivatives and derivatives of animal origin. Proanthocyanidins are flavonoids present in particular in grapes. Terpenoids are present in spices. Sterols, phytosterols and sterols esters are present in particular in vegetable oils, seeds, nuts and vegetables. Tocotrienols are present in particular in rice bran, barley, wheat, palm oil, rye and oats. Squalene is present in particular in fish liver, olive oil, wheat germ oil or rice bran oil. Finally, retinoids are present in particular in liver, egg yolk and dairy products.

In a preferred embodiment of the primary composition according to the invention, the lipophilic bioactive compound is obtained from tomatoes, for example tomato puree or a tomato extract. The presence of lycopene in tomatoes is advantageous for the present invention. The bioactive compound can also be a soybean extract. It is also possible to have a mixture of tomato extract and of soybean extract. These extracts are obtained by conventional methods, with the preferred tomato extract being a lipidic extract obtained by use of a solvent such as ethyl acetate, and the soybean extract being obtained from the ethanol/hot water extraction of soy which has been initially defatted by treatment by hexane.

The composition according to the invention can be provided in the form of a powder, liquid or gel.

As already mentioned above, the present invention provides a composition comprising a lipophilic bioactive compound which has a better bioavailability than the compound alone. Also, these compositions may be in the form of a highly water-dispersible composition, if the powder form is chosen. In this instance, the powder is dispersible in water at ambient temperature. Another feature of the invention is to protect and preserve the activity of the lipophilic bioactive compound with whey protein.

In the compositions according to the invention, the preferred additive for increasing bioactivity of the compound is whey protein, for example in the form of whey protein isolate. The term "whey protein" is understood to mean a product comprising at least 80% of whey proteins.

The primary composition according to the invention can additionally comprise vitamin E and vitamin C. Vitamin E (tocopherol) can be of exogenous or endogenous origin. If desired, vitamin C in any conventional form may be added to the composition.

The composition additionally comprises one or more of emulsifiers, stabilizers and other additives. Use is made of emulsifiers compatible in the food field, such as phospholipids, for example lecithin, polyoxyethylene sorbitan mono- or tristearate, monolaurate, monopalmitate, mono- or trioleate, a mono- or diglyceride. Use may also be made of any type of stabilizer that is known in the food business, in cosmetics or in pharmaceuticals. Use is made, as additives, of flavorings, colorants and any other additive known in the food business, in cosmetics or in pharmaceuticals. These emulsifiers, stabilizers and additives are added according to the final use of the primary composition.

In the primary composition, the lipophilic bioactive compound is preferably present in an amount of about 0.05 to 50% by weight of the composition and the whey protein is present in an amount of about 5 to 90% of the composition. Also, the whey protein and lipophilic bioactive compound may be present in a weight ratio of at least about 1:1 to 500:1, preferably from about 1.5:1 to 250:1 and more preferably about 2:1 to 20:1.

In a preferred embodiment of the invention, the primary composition comprises tomato oleoresin, soybean extract and whey protein. The term "tomato oleoresin" is understood to mean, in the present description, a lipid extract of the tomato plant, including carotenoids, such as lycopene, triglycerides, phospholipids, tocopherol and other less significant compounds. The term "soybean extract" is understood to mean a soybean extract comprising a high content of isoflavone. It is also possible to envisage other carotenoid-comprising plants, in particular melons, guavas, grapefruit, apricots, rosehips, carrots, peaches and oranges.

The present invention additionally relates to an oral composition comprising the primary composition described above in a foodstuff, in a food supplement, in a cosmetic preparation or in a pharmaceutical preparation.

This orally ingestible composition makes it possible to enhance the bioavailability of the lipophilic bioactive compound in the body and to slow down the ageing of the skin. Mention may be made, as foodstuff supplemented by the above primary composition, of yogurts, liquid drinks, chocolate, ice creams, cereals, chocolate powders, coffee, culinary products, such as mayonnaise, tomato puree or salad dressings, infant nutrition products, enteral nutrition products or pet foods. In this case, the powder is dissolved in the above-mentioned foods or drinks so as to have a daily intake of between about 0.001 and 50 mg of lipophilic bioactive compound, for example such as lycopene. A daily intake of the order of about 5 to 20 mg per day is preferably envisaged.

It is also possible to envisage, according to the invention, a food supplement in the form of sugar-coated tablets, pills, gelatin capsules, a syrup, a gel, a cream or lozenges with a dose of about 0.001 to 100% of the primary composition, which can then be taken directly with water or by any other known means. This supplement may also include a sweetener, a stabilizer, an additive, a flavoring or a colorant.

The oral composition can also be a cosmetic preparation comprising the primary composition and a compound active with respect to the skin known to a person skilled in the art.

The oral composition can also be a pharmaceutical preparation comprising the primary composition and a pharmaceutical compound, for example a compound in topical application or which can be orally ingested.

The invention also relates to a cosmetic composition comprising the primary composition described above. In this case, the content of primary composition is between $10^{-10}$ and 10%. The cosmetic composition preferably comprises between $10^{-8}$ and 5% of lipophilic bioactive compound.

This composition which can be used topically additionally comprises a fat or an oil which can be used in cosmetics, for example those mentioned in the CTFA work, Cosmetic Ingredients Handbook, Washington. It is also possible to add other cosmetically active ingredients. The composition additionally comprises a structuring agent and an emulsifier.

Other excipients, colorants, fragrances or opacifiers can also be added to the composition.

The present invention additionally relates to the use of the oral composition or of the cosmetic composition described above for protecting the tissues of the skin against ageing, in particular for inhibiting damage to the skin and/or mucous membranes by inhibiting collagenases and enhancing the synthesis of collagen.

The present invention additionally relates to the process for the preparation of the primary composition described above, in which the whey protein is mixed with the lipophilic bioactive compound.

In a first embodiment of the process according to the invention,
  the whey protein is dissolved in water,
  the lipophilic bioactive compound is dissolved in a solvent,
  the two solutions are mixed,
  the solvent is evaporated, and
  a dispersion is obtained.

In a first alternative form of the process according to the invention, a dispersion is obtained. In a second alternative form, the dispersion is heat-treated to produce a gel. And, in a third alternative form, the dispersion is dried by spraying or by lyophilization to produce a powder. The composition according to the invention may be directly usable as is or as a mixture, as will be explained below.

The whey protein is dissolved in water at a temperature in the region of or slightly greater than ambient temperature. An oleoresin which comprises between 1 and 40% of lycopene is used. The amounts are given as weight/weight. When the oleoresin is dissolved in the solvent, the ratio of the said oleoresin to the solvent is of the order of 1:1 to 1:900 by weight.

The solvent is any type of solvent compatible with the food business, cosmetics or pharmaceuticals. The solvent is preferably acetone, ethanol or isopropanol. When the aqueous phase is mixed with the solvent, a solvent/water ratio by volume of the order of 60/40 is chosen.

After mixing the two phases, the mixture is left to stand for 30 to 60 min at a temperature slightly higher than ambient temperature, for example of the order of 30° C., and the first operation is to drive off the solvent under a moderate vacuum. The term "moderate vacuum" is understood to mean a vacuum of between 200 and 300 mbar. If a powder is desired, the water is removed, either under vacuum or by spraying or by lyophilization. The term "vacuum" is understood to mean a vacuum of between 40 and 50 mbar. If a gel is desired, the emulsion is heated or any other technique known to a person skilled in the art for preparing the said gel is employed.

In a second embodiment of the process according to the invention,
- the lipophilic bioactive compound is mixed with a solvent,
- the composition obtained is mixed with the whey protein powder, and
- the solvent is evaporated to produce a powder composition.

The solvent used is the same as that mentioned above.

In a third embodiment, the lipophilic bioactive compound, either in the oleoresin form or in the powder form or in any other dry form (for example, the oleoresin is absorbed on a support), is mixed directly with the whey powder (optionally comprising a soybean extract) to produce the primary composition according to the invention.

EXAMPLES

The continuation of the description is now made with reference to the examples which illustrate preferred embodiments of the invention.

Example 1

Preparation of the Composition in the Powder Form 13.3 kg of whey protein isolate are dissolved in 330 l of demineralized water and the mixture is stirred for 6 hours at 25-30° C. Separately, 550 g of oleoresin from Lycored, comprising 6% of lycopene, are mixed in 438 l of acetone and the mixture is stirred.

The 2 solutions are subsequently mixed for 60 min at 30° C. The final mixture is moderately heated and the acetone is driven off at a moderate pressure. Finally, water is partially driven off at a pressure of 40-50 mbar. An aqueous solution of 200 kg of whey protein isolate and of oleoresin is obtained.

This solution is subsequently spray dried.

Starting from this powder, tests were carried out with people who were daily given this powder comprising 25 mg of lycopene and other carotenoids present in the oleoresin and 12.5 g of whey proteins: the powder was taken by dissolving it in apple juice. In comparison with the reference, which was tomato puree comprising the same amount of lycopene, a bioavailability of the lycopene starting from the powder according to the invention equal to that starting from the tomato puree was observed. This study was carried out over a period of 8 weeks. It should be remembered that tomato puree is regarded by a person skilled in the art as the product having the best bioavailability of lycopene. This demonstration was carried out by quantitative determination of the lycopene in the blood plasma.

Example 2

Preparation of Sugar-Coated Tablets

A dispersion of 550 g of oleoresin of Example 1 with an emulsifier in ethanol is prepared. This dispersion is mixed with 1 100 g of whey protein and 1 100 g of soybean extract (comprising 40% of isoflavone). The solvent is driven off to produce a powder.

The powder thus obtained is mixed with ascorbic acid and other additives, such as one or more sweeteners, thickeners and food additives, making possible preparation in the form of sugar-coated tablets. The mixture obtained is subsequently sugar-coated.

Sugar-coated tablets of the order of 700 mg, comprising 33 mg of lycopene, 70 mg of soybean extract, 70 mg of whey protein, 40 mg of ascorbic acid, the remainder being sweeteners, thickeners and food additives, to arrive at 700 mg, are thus prepared.

Example 3

Cosmetic Composition

A milk for the face is prepared comprising 7% of liquid petrolatum, 2% of powder according to Example 1, 3% of glyceryl monostearate, polyethylene glycol stearate, 0.4% of carboxyvinyl polymer, 0.7% of stearyl alcohol, 3% of soybean proteins, 0.4% of NaOH and a preservative, and the remainder to 100 being water.

Example 4

Cosmetic Composition

A gel for the face is prepared comprising 10% of glycerol, 2% of powder according to Example 1, 1% of disodium cocoamphodiacetate and a preservative, and the remainder to 100 being water.

Example 5

Study of the Stability of Lycopene

It is known that light and oxygen cause lycopene to decompose. An aqueous-phase analysis of the stability of lycopene alone and of lycopene in combination with the whey protein according to the invention was carried out. After one day in the aqueous phase for lycopene alone, only 40% of the lycopene remains, whereas, with the whey, virtually 90% of it remains. After two days, 60% of it remains with the whey, whereas the lycopene is virtually completely decomposed if it is alone.

A protective effect on the lycopene by the whey protein therefore clearly exists.

The invention is claimed as follows:

1. A method for increasing bioavailability of a lipophilic bioactive compound to a subject upon administration, the method comprising:
   associating a whey protein with the lipophilic bioactive compound by dissolving the whey protein in water to form a first solution, dissolving the lipophilic bioactive compound in a solvent to form a second solution, combining the first and second solutions, and evaporating the solvent to form a primary composition as a dispersion, the whey protein present in an amount sufficient to increase the bioavailability of the lipophilic bioactive compound to the subject upon administration; and administering the primary composition to the subject, wherein increased amounts of the lipophilic bioactive compound are released as compared to lipophilic compositions that do not include whey protein.

2. The method according to claim 1, wherein the solvent is acetone, ethanol, isopropanol or a mixture thereof.

3. The method according to claim 1, wherein the dispersion is heat-treated to produce the primary composition in gel form.

4. The method according to claim 1, wherein the dispersion is dried by spraying or lyophilization to produce the primary composition in powder form.

5. The method according to claim 1, wherein the solvent is acetone, ethanol, isopropanol or a mixture thereof.

6. The method according to claim 1, wherein the lipophilic bioactive compound is obtained, extracted, enriched or purified from a plant, microorganism, yeast or product of animal origin.

7. The method according to claim 6, wherein the lipophilic bioactive compound is obtained, extracted, enriched or purified from tomatoes, soya, green tea, green coffee beans, spices, grapes, cocoa, ginger or cereals, is produced from a bacterium, or is produced from a liver extract or a milk fraction.

8. The method according to claim 1, wherein the lipophilic bioactive compound is selected from the group consisting of: a carotenoid, polyphenol, lipophilic vitamin, flavonoid, isoflavone, curcuminoid, ceramide, proanthocyanidin, terpenoid, sterol, phytosterol, sterol ester, tocotrienol, squalene, or retinoid, alone or as a mixture.

9. The method according to claim 1, wherein the lipophilic bio active compound is a tomato extract, a soybean extract or a mixture thereof.

10. The method according to claim 1, which further comprises adding at least one of vitamin C, tocopherol, an emulsifier, a stabilizer or another additive to the primary composition.

11. The method according to claim 1, wherein the lipophilic bioactive compound is present in an amount of about 0.05 to 50% by weight of the primary composition and the whey protein is present in an amount of about 5 to 90% of the primary composition.

12. The method according to claim 11, wherein the whey protein and the lipophilic bioactive compound are present in the primary composition in a weight ratio of about 1:1 to 500:1.

13. The method according to claim 1, wherein the primary composition is administered to the subject by: adding the primary composition to a foodstuff, a food supplement or a pharmaceutical preparation; and orally administering the foodstuff, food supplement or pharmaceutical preparation to a subject such that about 0.001 mg to 50 mg of the lipophilic bioactive compound is administered.

14. The method according to claim 13, wherein the primary composition is added to a foodstuff that comprises a yogurt, a liquid drink, a chocolate-containing product, an ice cream, cereal, coffee or animal food.

15. The method according to claim 13, wherein the primary composition is added to a food supplement that further comprises at least one of a sweetener, a stabilizer, a flavoring or a colorant and is provided in the form of sugar-coated tablets, pills, gelatin capsules, a syrup, a gel or a cream.

16. The method according to claim 13, wherein the content of the primary composition is between about 0.001 and 100% of the foodstuff, food supplement or pharmaceutical preparation.

17. The method according to claim 13, wherein the content of the primary composition is between about 10 and 50% of the foodstuff, food supplement or pharmaceutical preparation.

* * * * *